US009719932B1

(12) United States Patent
Shaughnessy et al.

(10) Patent No.: US 9,719,932 B1
(45) Date of Patent: Aug. 1, 2017

(54) CONFINED ILLUMINATION FOR SMALL SPOT SIZE METROLOGY

(71) Applicant: KLA-Tencor Corporation, Milpitas, CA (US)

(72) Inventors: Derrick Shaughnessy, San Jose, CA (US); Michael S. Bakeman, San Jose, CA (US); Guorong V. Zhuang, San Jose, CA (US); Andrei V. Shchegrov, Campbell, CA (US); Leonid Poslavsky, Belmont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 14/532,971

(22) Filed: Nov. 4, 2014

Related U.S. Application Data

(60) Provisional application No. 61/899,401, filed on Nov. 4, 2013.

(51) Int. Cl.
| | |
|---|---|
| *G01N 21/00* | (2006.01) |
| *G01N 21/67* | (2006.01) |
| *G01N 21/95* | (2006.01) |
| *H01S 3/0915* | (2006.01) |

(52) U.S. Cl.
CPC ......... *G01N 21/67* (2013.01); *G01N 21/9501* (2013.01); *H01S 3/0915* (2013.01)

(58) Field of Classification Search
CPC ........... G01N 21/9501; G01N 21/8806; G01N 21/6454; G01N 21/956; G01N 2021/1736; G01N 2021/6419; G01N 2021/6421; G01N 2021/8405; G01N 2021/8825; G01N 2021/95676; G01N 21/05; G01N 21/31; G01N 21/552
See application file for complete search history.

(56) References Cited

U.S. PATENT DOCUMENTS

| | | | |
|---|---|---|---|
| 7,368,741 B2 | 5/2008 | Melnychuk et al. | |
| 7,435,982 B2 | 10/2008 | Smith | |
| 7,705,331 B1* | 4/2010 | Kirk | ............... G01N 21/956 250/306 |
| 7,786,455 B2 | 8/2010 | Smith | |
| 7,989,786 B2 | 8/2011 | Smith et al. | |
| 8,148,900 B1* | 4/2012 | Kirk | ............... G01N 21/8806 313/607 |

(Continued)

*Primary Examiner* — Michael P Stafira
(74) *Attorney, Agent, or Firm* — Spano Law Group; Joseph S. Spano (57) ABSTRACT

Methods and systems are described herein for producing high radiance illumination light for use in semiconductor metrology based on a confined, sustained plasma. One or more plasma confining circuits introduce an electric field, a magnetic field, or a combination thereof to spatially confine a sustained plasma. The confinement of the sustained plasma decreases the size of the induced plasma resulting in increased radiance. In addition, plasma confinement may be utilized to shape the plasma to improve light collection and imaging onto the specimen. The induced fields may be static or dynamic. In some embodiments, additional energy is coupled into the confined, sustained plasma to further increase radiance. In some embodiments, the pump energy source employed to sustained the plasma is modulated in combination with the plasma confining circuit to reduce plasma emission noise.

11 Claims, 6 Drawing Sheets

(56) References Cited

U.S. PATENT DOCUMENTS

| | | |
|---|---|---|
| 8,294,382 B2 | 10/2012 | DeVincentis et al. |
| 8,319,439 B2 | 11/2012 | Hollingsworth et al. |
| 8,436,546 B2 | 5/2013 | DeVincentis et al. |
| 2004/0106213 A1* | 6/2004 | McLaughlin ...... G01N 33/0047 436/171 |
| 2006/0091109 A1* | 5/2006 | Partlo ...................... B08B 7/00 216/63 |
| 2011/0205529 A1* | 8/2011 | Gross ........................ G01J 3/10 356/51 |
| 2013/0114085 A1 | 5/2013 | Wang et al. |
| 2013/0169966 A1* | 7/2013 | Shchegrov ......... G01N 21/4738 356/369 |
| 2013/0234597 A1* | 9/2013 | Kusunose ................. H01J 1/52 315/111.21 |
| 2013/0342105 A1* | 12/2013 | Shchemelinin ... H01J 37/32055 315/111.21 |

\* cited by examiner

CONFINED ILLUMINATION FOR SMALL SPOT SIZE METROLOGY

CROSS REFERENCE TO RELATED APPLICATION

The present application for patent claims priority under 35 U.S.C. §119 from U.S. provisional patent application Ser. No. 61/899,401, entitled "Method And Systems For Providing Illumination For Small Spot Metrology System," filed Nov. 4, 2013, the subject matter of which is incorporated herein by reference.

TECHNICAL FIELD

The described embodiments relate to optical metrology and inspection systems for microscopy, and more particularly to optical metrology and inspection systems involving plasma based radiation sources.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Metrology processes are used at various steps during a semiconductor manufacturing process to detect defects on wafers to promote higher yield. In the field of semiconductor metrology, a metrology tool includes an illumination system which illuminates a target, a collection system which captures relevant information provided by the illumination system's interaction (or lack thereof) with a target, and a processing system which analyzes the information collected using one or more algorithms. Metrology tools can be used to measure structural and material characteristics (e.g., material composition, dimensional characteristics of structures and films such as film thickness and/or critical dimensions of structures, overlay, etc.) associated with various semiconductor fabrication processes. These measurements are used to facilitate process controls and/or yield efficiencies in the manufacture of semiconductor dies.

Traditionally, measurement targets are designed to fit within a scribe line between die on a semiconductor wafer. However, more recently, measurement targets are designed to fit within the die area. As measurement targets decrease in size, the size of the illumination spot projected onto the specimen should also decrease. The size of the illumination spot must be small enough to ensure that the detected light-sample interactions originate within the measurement target of interest and are not contaminated by light that interacts with structures outside the region of interest.

Traditionally, metrology systems are designed to optimize the illumination profile projected onto the specimen by appropriate optical design in both the illumination and collection paths (i.e., magnification, apodization, diffraction control, etc.). Unfortunately, these techniques generally reduce the amount of light projected onto the specimen. For example, magnification reduces the solid angle of collection from the source. Due to the conservation of etendue, the usable spectral power density from the source is also reduced. In another example, apodization tailors the source spatial intensity distribution projected onto the specimen to reduce contamination from outside the region of interest. In yet another example, field stops reduce the lateral extent of the source that is imaged onto the specimen. Each of these measures inherently reduces the brightness of the illumination system.

In some examples, longer integration times are used to accommodate the light lost due to traditional optical design features employed to reduce the illumination spot size (e.g., magnification, apodization, etc.). However, longer integration times increase the system sensitivity to lower frequency noise sources. In some examples, low frequency noise sources become dominant and further increases in integration time no longer improves the system signal to noise ratio. In addition, the increase in signal acquisition time is not desirable from a product perspective as it reduces system throughput and thus increases cost of ownership of the system.

In some examples, current metrology systems employ an electrode-based, relatively high intensity discharge arc lamp to generate illumination light. These arc lamps include an anode and cathode to excite a working gas (typically xenon or mercury gas) contained within a chamber of the lamp. An electrical discharge is generated between the anode and cathode to provide power to the excited (e.g., ionized) gas to sustain light emission from the ionized gas during operation of the light source. However, these light sources have a number of disadvantages. For example, electrode based, relatively high intensity discharge arc lamps have radiance limits and power limits due to electrostatic constraints on current density from the electrodes, the limited emissivity of gases as black body emitters, the relatively rapid erosion of electrodes made from refractory materials due to the presence of relatively large current densities at the cathodes, and the inability to control dopants (which can lower the operating temperature of the refractory cathodes) for relatively long periods of time at the required emission current. As a result, state of the art xenon-based arc lamps typically generate light with a color temperature that is limited to approximately 6,000 degrees Kelvin.

The use of electrodes limits the amount of energy that can be transferred to the plasma as there is a finite surface area over which energy is transferred from the electrode to the plasma. The proximity of the electrode to the plasma results in electrode surface bombardment by highly energetic particles. This causes sputtering of the electrode material that leaves deposits of the electrode material on the surface of optical components. This reduces transmission and the radiance of the illumination delivered to the metrology system. In addition, the proximity of the electrode to the plasma increases the electrode temperature. This may alter the material properties of the electrode, which, in turn, influences plasma properties.

In some other examples, laser sustained plasma based light sources have been developed. An exemplary laser sustained plasma system is described in U.S. Pat. No. 7,786,455 assigned to Energetiq Technology Inc. In one example, a xenon lamp is ignited with a high voltage pulse applied through electrodes. Once started, the plasma is continuously sustained with an energetic laser beam focused to a small volume inside the Xenon gas envelope. However, laser sustained plasma light sources also face significant limitations. The laser sustained plasma develops a temperature gradient across the plasma (i.e., hotter on the inside, cooler on the outside) that causes self-absorption; particularly absorption of short wavelength light. As a result, it is difficult to increase the plasma temperature beyond approximately 12,000-15,000 degrees Kelvin. Moreover, an increase in laser power generally results in a larger plasma size that has a diminishing impact on color temperature and radiance.

In some other examples, light sources employing laser produced plasma have been developed for lithographic applications. An exemplary extreme ultraviolet (EUV) light source is described in U.S. Pat. No. 7,368,741 assigned to Cymer, Inc. In one example, a working gas at low pressure is pre-ionized by a radiofrequency coil, ignited with a focused laser beam, and sustained by a combination of the focused laser beam and electrical discharge to generate a pinch plasma that emits EUV light. Generation of illumination suitable for EUV lithography requires emission along atomic lines, rather than broadband emission. As a result, EUV illumination sources generate plasma in a low pressure (i.e., vacuum) environment to minimize reabsorption of the EUV emission. The low pressure environment allows the plasma to spread over a large volume. If relatively high pressures were employed (e.g., 0.5 atmosphere, or greater), these sources would fail to generate any useable amount of EUV light. Large plasma volumes are acceptable for an EUV source that focuses on the generation of as much EUV emission along atomic lines as possible. However, in a metrology application, high radiance, broadband radiation is required. The large plasmas generated by systems designed for EUV emission suffer from low brightness and narrow band emission that does not fulfill the requirement for broadband, high brightness illumination in metrology applications.

Existing illumination sources are limited in radiance and color temperature for small spot size metrology applications. Thus, improved methods and systems for generating and extracting high radiance, broadband light at suitable flux levels are desired.

SUMMARY

Methods and systems are described herein for producing high radiance illumination light for use in semiconductor metrology based on a confined, sustained plasma. More specifically, one or more plasma confining circuits introduce an electric field, a magnetic field, or a combination of an electric field and a magnetic field that spatially confine a sustained plasma. The confinement of the sustained plasma decreases the size of the induced plasma resulting in increased radiance. In addition, plasma confinement may be utilized to shape the plasma to improve light collection and imaging onto the specimen.

In one aspect, a high radiance illumination source for use in semiconductor metrology includes a system or systems for igniting and sustaining a plasma and one or more plasma confining circuits that introduce an electric field, a magnetic field, or a combination of an electric field and a magnetic field to spatially confine the sustained plasma.

In some embodiments, a plasma confining circuit introduces an electric field to spatially confine a sustained plasma. In one example, the plasma confining circuit includes two spherically shaped grids, one arranged within the other. A voltage source generates an electric potential across the two spherically shaped grids that induces an electrical field oriented radially between the spherically shaped grids and confines the plasma. In some embodiments, the voltage source supplies a fixed voltage, and hence generates a static electric field. In some other embodiments, the voltage source supplies a time-varying voltage that induces a dynamic electric field.

In some embodiments, a plasma confining circuit introduces a magnetic field to spatially confine a sustained plasma. In one example, the plasma confining circuit includes a coil with windings turned around the plasma. A current source drives a current through the coil that induces a magnetic field that confines the plasma. In some embodiments, the current source supplies a fixed current, and thus generates a static magnetic field. In some other embodiments, the current source supplies a time-varying current that induces a dynamic magnetic field.

In general, the elements employed to confine a sustained plasma (e.g., electrically conductive wire grids, wire coils, etc.) may be located within the plasma chamber containing the plasma or outside the plasma chamber. It may be advantageous to locate the confinement circuit elements outside of the plasma chamber to improve reliability. However, in some embodiments it may be desirable to locate elements of the confinement circuit within the plasma chamber in close proximity to the plasma to enhance the confining effect of the induced fields.

In another aspect, one or more plasma confining circuits of a confined, sustained plasma (CSP) light source confines the plasma to a substantially fixed size as the pump energy supplied to sustain the plasma is increased. By way of non-limiting example, a pump laser of a CSP light source is controlled to increase the plasma temperature of the plasma while the plasma is confined by a plasma confining circuit. In some other examples, one or more plasma pump circuits provide additional pump energy to a confined, sustained plasma by an inductive coupling, a capacitive coupling, or both. In some embodiments, RF or microwave power is capacitively or inductively coupled to the plasma to increase the plasma temperature.

In another further aspect, a system or systems for sustaining a plasma and one or more plasma confining circuits of a CSP light source are modulated in combination to minimize plasma emission noise. Combining pump energy modulation with modulation of a plasma confining circuit (i.e., modulation of the plasma shape) generates a set of extended modulation frequencies to optimize stable photon emission radiance.

In yet another further aspect, a system or systems for confining a plasma may be employed to shape the plasma to avoid damage to elements of the CSP light source. For example, the plasma may be shaped by one or more plasma confining circuits to maintain a particular distance between the confined, sustained plasma and a window of the plasma chamber.

A metrology system incorporating a high radiance, confined, sustained plasma light source is able to more efficiently image the smaller sized plasma onto a specimen over a smaller illumination spot size. In some embodiments, the illumination spot size has a diameter of 25 micrometers or less, three sigma, for wavelengths less than 900 nanometers. In some embodiments, the illumination spot size has a diameter of 10 micrometers or less, three sigma, for wavelengths less than 900 nanometers.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems are described herein for producing high radiance illumination light for use in semiconductor metrology based on a confined, sustained plasma. More specifically, one or more plasma confining circuits introduce an electric field, a magnetic field, or a combination of an electric field and a magnetic field that spatially confines a plasma. The confinement of the sustained plasma decreases the size of the induced plasma resulting in increased radiance. In some embodiments, the plasma is sustained by a pump laser.

In general it is beneficial to have as many photons as possible interact with the specimen in the region of interest, in the spectral range of interest, and in as short a period of time as possible to improve the system signal to noise ratio. A confined, sustained plasma light source increases the number of photons per unit solid angle and per unit projected area over a broad spectral range. In addition, a metrology system incorporating a high radiance, confined, sustained plasma light source is able to more efficiently image the smaller sized plasma onto a specimen over a smaller illumination spot size. In some embodiments, the illumination spot size has a diameter of 25 micrometers or less, three sigma, for wavelengths less than 900 nanometers. In some embodiments, the illumination spot size has a diameter of 10 micrometers or less, three sigma, for wavelengths less than 900 nanometers.

In general, any system or combination of systems for initiating a plasma may be contemplated within the scope of this patent document. By way of non-limiting example, a plasma may be ignited by an arc, an inductively coupled system, a capacitively coupled system, a pump laser system, or a combination of these systems. In addition, any method or methods of sustaining a plasma may be contemplated within the scope of this patent document. By way of non-limiting example, a plasma may be sustained by an inductively coupled system, a capacitively coupled system, a pump laser system, or a combination of these systems.

In general, significantly more power is required to initiate a plasma than to sustain the plasma. As such, a confined, sustained plasma light source as described herein may include different energy sources to initiate and sustain the plasma. In some embodiments, an electrode or electrodes provide energy to initiate the plasma. Once the plasma is initiated, the voltage applied to the electrodes is removed. In these embodiments, the electrodes are designed to be sufficiently far from the plasma to minimize their impact on lamp operating performance and reliability. In some other embodiments, a high power laser (e.g., pulsed laser) is focused coincident with the focal point of the sustaining energy source and contributes pump energy only during the plasma ignition process. In some other embodiments, capacitively or inductively coupled energy sources are employed solely for the purposes of initiating the plasma. In a preferred embodiment, a continuous wavelength (CW) laser system is employed to sustain the plasma.

In one aspect, a high radiance illumination source for use in semiconductor metrology includes a system or systems for igniting and sustaining a plasma and one or more plasma confining circuits that introduce an electric field, a magnetic field, or a combination of an electric field and a magnetic field to spatially confine the sustained plasma.

In some embodiments, the shape of a laser sustained plasma is optimized for sample illumination based in part on laser power, laser source shape, pump laser NA, and absorption of the pump laser by the working gas. In a further aspect, the shape of the laser sustained plasma is confined by one or more plasma confining circuits that introduce an electric field, a magnetic field, or a combination of an electric field and a magnetic field. Plasma confinement may be utilized to increase source radiance as well as improve overall system performance by tailoring the plasma shape to optimize collected power and illumination spot size. In some embodiments, the plasma shape optimizes the transmission of light through a fiber coupling from the plasma illumination source to the system illumination optics.

Figure 1:
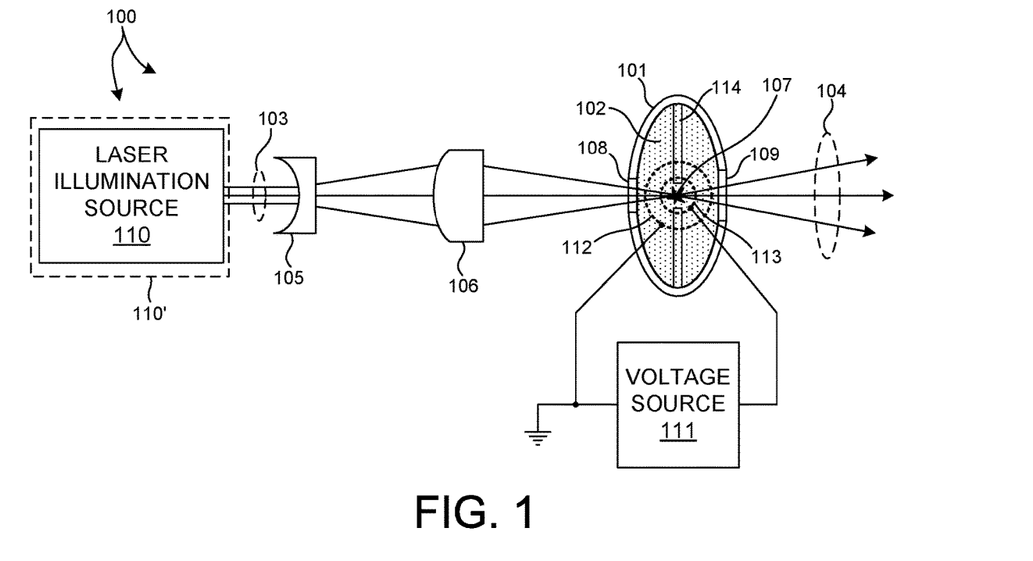
FIG. 1 illustrates a confined, sustained plasma (CSP) light source that includes a plasma confining circuit that introduces an electric field to spatially confine a sustained plasma in one embodiment.

FIG. 1 illustrates an embodiment of a Confined, Sustained Plasma (CSP) light source 100 configured in accordance with at least one aspect of the present invention. CSP light source 100 includes a set of electrodes 114 configured to ignite a plasma 107 within plasma chamber 101. CSP light source 100 includes a pump energy source 110'. In the embodiment depicted in FIG. 1, pump energy source 110' is laser illumination source 110 configured to supply energy to sustain the plasma 107 within plasma chamber 101. Laser illumination source 110 is configured to generate an output beam 103 that passes through a beam expanding optic 105 and a condensing optic 106 configured to focus the laser illumination at the location of plasma 107 with high numerical aperture (NA). In some embodiments, the optical elements are configured to generate a NA greater than 0.6. To locate condensing optic 106 within a reasonable working distance from plasma 107 (e.g., few centimeters) at high NA (e.g., greater than 0.6), a beam expanding optic 105 is employed. In some embodiments, beam expanding optic 105 is configured to expand the diameter of the incoming beam by 200 times, or more, at incidence with the condensing optic 106.

In the depicted embodiment, plasma chamber 101 is a reflective chamber configured to collect light radiated from the plasma for illumination of a specimen undergoing measurement. Plasma chamber 101 includes at least one window 108 formed from a material (e.g., glass) that is substantially transparent to at least a portion of the pulsed output beam 103 generated by laser illumination source 110. Similarly, plasma chamber 101 includes at least one window 109 that is also substantially transparent to at least a portion of the collectable illumination 104 (e.g., IR light, visible light, ultraviolet light) emitted by the plasma 107 ignited within the plasma chamber 101. For example, the wall 101 may be transparent to a particular spectral region of the broadband emission 104 from the plasma 107.

In some embodiments, plasma chamber 101 may be a bulb formed from a variety of glass or crystalline materials. In one embodiment, plasma chamber 101 is a glass bulb that may be formed from fused silica glass. In some embodiments, the plasma chamber 101 may be formed from a low OH content fused synthetic quartz glass material. In other embodiments, the plasma chamber 101 may be formed from a high OH content fused synthetic silica glass material. For example, the plasma chamber 101 may include, but is not limited to, SUPRASIL 1, SUPRASIL 2, SUPRASIL 300, SUPRASIL 310, HERALUX PLUS, and HERALUX-VUV. In some embodiments, a glass material forming the plasma chamber 101 may be doped with fluorine, hydrogen, etc. Various glasses suitable for implementation in the plasma chamber of the present invention are discussed in detail in A. Schreiber et al., Radiation Resistance of Quartz Glass for VUV Discharge Lamps, J. Phys. D: Appl. Phys. 38 (2005), 3242-3250, which is incorporated herein in the entirety. In some embodiments, the plasma chamber 101 may be formed from a crystalline material such as a crystalline quartz material, a sapphire material, calcium fluoride, or magnesium fluoride.

As an important component in the optical illumination system, the nominal shape, dimensional tolerances, and material composition of window 109, or a plasma bulb envelope, are selected to minimize aberrations introduced into the image of the plasma projected onto the specimen under measurement and optimize transmission in the wavelength region of interest. For example, in some embodiments sapphire is selected as a window material or cell material to optimize transmission for ultraviolet output. In some embodiments, optical or acousto-optic filters are located in the optical path from the plasma source to the specimen to filter out radiation for desired applications. For example, a set of filters (e.g., a set of filters arranged on a filter wheel) may be required to produce selectable spectral outputs in an angularly resolved reflectometer. In another example, selectable apodizing elements may be added to filter angular content generated by CSP light source 100.

In the illustrated embodiment, plasma chamber 101 has an ellipsoidal shape. However, in general, many other shapes may be contemplated. For example, plasma chamber 101 may have a cylindrical shape with spherical ends. In some embodiments, plasma chamber 101 includes any of a substantially spherical shape, a substantially cylindrical shape, a substantially ellipsoidal shape, and a substantially prolate spheroid shape. These shapes are provided by way of non-limiting example. Many other shapes may be contemplated.

In general, the shape of plasma chamber 101 is selected to optimize energy coupling into the plasma. In examples employing a pump laser source (e.g., CSP 100 depicted in FIG. 1), aberrations introduced into the imaging of the pump laser are minimized to ensure the tightest possible focus. In examples employing inductively or capacitively coupled plasmas, the shape of the plasma chamber 101 optimizes the coupling of radio frequency (RF) or microwave energy into the plasma. In some embodiments, an RF current is passed through a coil surrounding a plasma chamber to induce a time varying magnetic field and generate an inductively coupled plasma. In these embodiments, the plasma chamber is constructed of materials with high magnetic permeability and the coil is located as close to the plasma chamber possible to maximize the induced magnetic field. In some other embodiments, a high frequency voltage is supplied across a set of plates arranged on opposite sides of a plasma chamber to induce a time varying electric field and generate a capacitively coupled plasma. In these embodiments, the plasma chamber is constructed from materials with a high electric permittivity to maximize the induced electric field.

In some embodiments, working gas 102 is not contained in a bulb, but is included in a reflective chamber configured to collect light radiated from the plasma for illumination of a specimen undergoing measurement. In these embodiments, the optical path from the plasma to the specimen under inspection includes reflective elements, but does not include transmissive elements. These embodiments may be preferred when transmission of short wavelength light (e.g., less than 200 nanometers) is desired without the optical losses that are inherent in the transmission of short wavelength light through solid media (e.g., lenses, windows, etc.).

The transition from an ordinary state of matter to a plasma state depends on the ionization energy of the working gas or gas mixture. This, in turn, depends on the electron configuration of the working gas or gas mixture. In some embodiments, xenon gas is selected as working gas 102 due to its low ionization energy. In some embodiments, working gas 102 is pure xenon gas. In some other embodiments, working gas 102 includes xenon gas mixed with one or more other gaseous species.

In a further aspect, working gas 102 also includes spurious amounts of a secondary species, such as a metal vapor. The presence of these species may facilitate break-down at lower electromagnetic field strength. In some embodiments, working gas 102 includes xenon gas mixed with a small amount of radio-active material.

In general, the plasma chamber 101 may be filled with any gas or combination of gases suitable for use in a sustained plasma light source including an inert gas (e.g., noble gas or non-noble gas) or a non-inert gas (e.g., mercury vapor) or their mixtures. By way of non-limiting example, the working gas may include any one or combination of Ar, Kr, Xe, He, Ne, $N_2$, $Br_2$, $I_2$, $H_2O$, $O_2$, $H_2$, $CH_4$, NO, $NO_2$, $CH_3OH$, $C_2H_5OH$, $CO_2$, $NH_3$, Fluorine, Fluorine dimers, Chlorine, Chlorine dimers, one or more metal halides, a Ne/Xe mixture, an Ar/Xe mixture, a Kr/Xe mixture, an Ar/Kr/Xe mixture, an ArHg mixture, a KrHg mixture, and a XeHg mixture, mercury, nitrogen trifluoride, sulfur hexafluoride, a rare gas, a rare earth gas, a transitional metal vapor, a halide vapor, or some combination thereof. Alternatively, the plasma could be generated from a solid or liquid target (e.g., mercury). The gas or target material may be selected to optimize plasma emission for a select application based on measurement criteria such as defect sensitivity. In general, the present invention should be interpreted to extend to any light pumped plasma generating system and should further be interpreted to extend to any type of working gas suitable for sustaining a plasma within a plasma chamber.

In one aspect, a CSP light source includes a plasma confining circuit that introduces an electric field to spatially confine a sustained plasma. FIG. 1 depicts a CSP light source 100 that includes a plasma confining circuit that introduces an electric field to spatially confine a sustained plasma 107 in one embodiment. As depicted in FIG. 1, the plasma confining circuit includes two spherically shaped grids, one arranged within the other. In some embodiments, each spherically shaped grid is constructed of tungsten. In addition, a voltage source 111 generates an electric potential across the two spherically shaped grids 112 and 113. As depicted in FIG. 1, a ground node of voltage source 111 is coupled to the outer spherically shaped grid 112 and a voltage node of voltage source 111 is coupled to the inner spherically shaped grid 113. In this manner, voltage source 111 generates an electrical field oriented radially between spherically shaped grid 112 and spherically shaped grid 113.

In some embodiments, voltage source 111 supplies a fixed voltage, and hence generates a static electric field across spherically shaped grid 112 and spherically shaped grid 113. The spherically symmetric electric field accelerates the plasma ions or electrons (depending on polarity) radially inward. The plasma ions or electrons are thus contained in the center of the symmetric electric field. In this manner, the electrons or ions of plasma 107 are contained within the inner spherically shaped grid 113, thus containing plasma 107.

In some other embodiments, voltage source 111 supplies a time-varying voltage, and hence generates a dynamic electric field across spherically shaped grid 112 and spherically shaped grid 113. In this manner, the electrons of plasma 107 and the ions of plasma 107 are alternately contained within the inner spherically shaped grid 113, thus containing plasma 107.

As depicted in FIG. 1, CSP light source 100 includes a plasma confining circuit that includes two spherically shaped grids, one arranged within the other. In another embodiment, a CSP light source 100 includes a plasma confining circuit that includes two cylindrically shaped grids, one arranged within the other. A voltage source generates an electrical field oriented radially between each cylindrically shaped grid in a manner analogous to that described with reference to FIG. 1.

Figure 2:
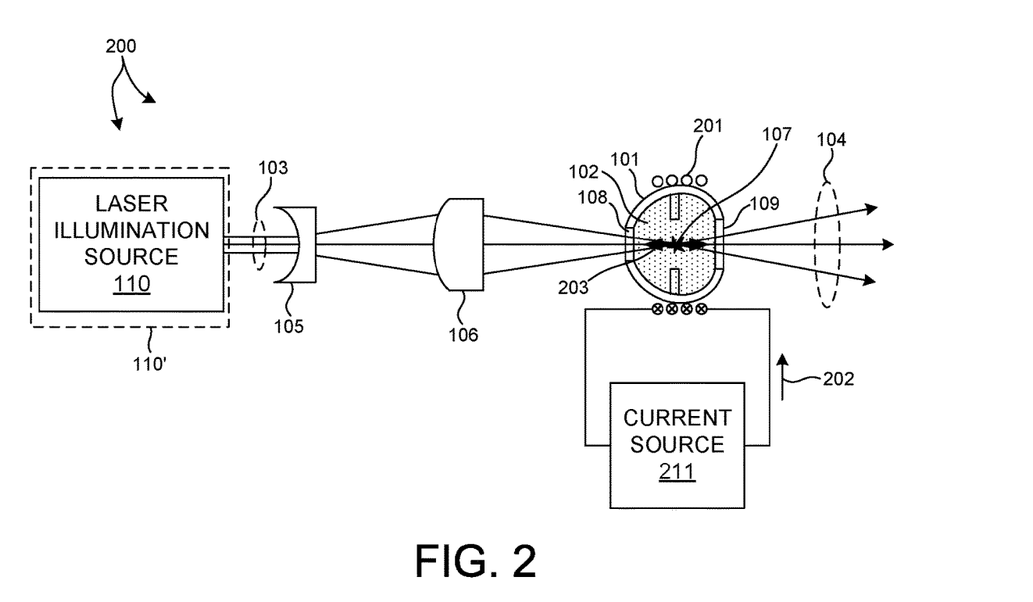
FIG. 2 illustrates a CSP light source that includes a plasma confining circuit that introduces a magnetic field to spatially confine a sustained plasma in one embodiment.

FIG. 2 depicts a CSP light source 200 that includes a plasma confining circuit that introduces a magnetic field to spatially confine a sustained plasma 107 in one embodiment. In the embodiment depicted in FIG. 2, like numbered elements are as described with reference to FIG. 1. As depicted in FIG. 2, the plasma confining circuit includes a coil 201 having windings turned around plasma 107. Current source 211 drives a current 202 through coil 201 and generates a magnetic field across plasma 107 in the direction indicated by arrow 203. Electrons and ions of plasma 107 follow helical paths around the magnetic field line indicated by arrow 203, thus containing plasma 107 in the radial direction.

In some embodiments, current source 211 supplies a fixed current, and hence generates a static magnetic field. In this manner, the electrons and ions of plasma 107 are contained in the radial direction, perpendicular to the magnetic field line indicated by arrow 203.

In some other embodiments, current source 211 supplies a time-varying current, and hence generates a dynamic magnetic field. In this manner, the electrons and ions of plasma 107 are contained in the radial direction and are driven in alternate directions along the axial direction, and are thus contained within the length of the coil in the axial direction.

As depicted in FIG. 2, CSP light source 200 includes a plasma confining circuit that includes a cylindrically wound coil. Passing current through the coil generates a magnetic field in the axial direction of the cylindrically wound coil. In another embodiment, a static magnetic field is generated by a set of permanent magnets arranged to generate a magnetic field in the desired direction, and thus confine the sustained plasma in a manner analogous to that described with reference to FIG. 2. In some embodiments, a dynamic magnetic field is generated by moving (e.g., rotating) a set of permanent magnets around the sustained plasma to generate a dynamic magnetic field to confine the sustained plasma.

Figure 3:
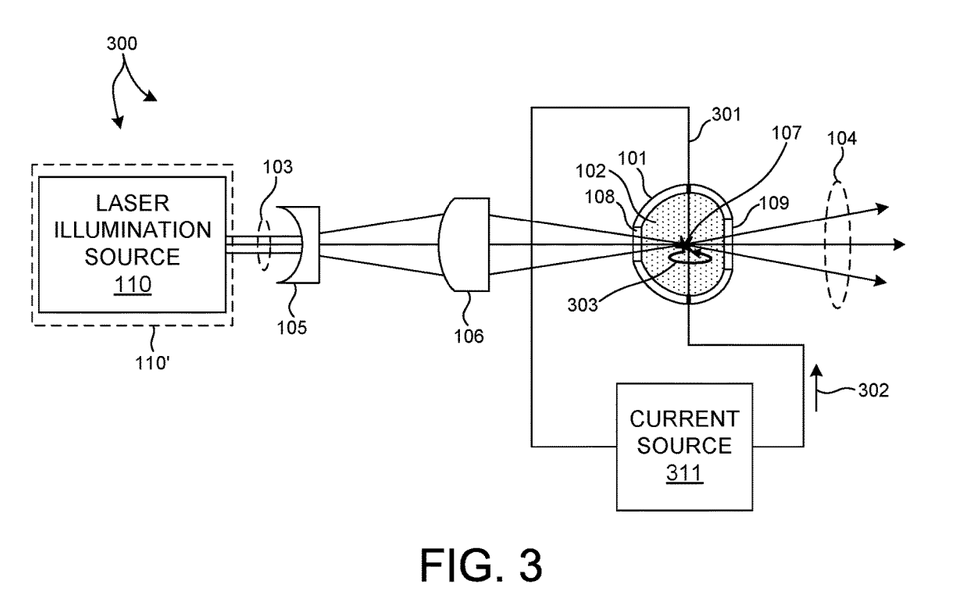
FIG. 3 illustrates a CSP light source that includes a plasma confining circuit that introduces a magnetic field to spatially confine a sustained plasma in another embodiment.

FIG. 3 depicts a CSP light source 300 that includes a plasma confining circuit that introduces a magnetic field to spatially confine a sustained plasma 107 in another embodiment. In the embodiment depicted in FIG. 3, like numbered elements are as described with reference to FIG. 1. As depicted in FIG. 3, the plasma confining circuit includes a wire 301 passed through the vicinity of plasma 107. Current source 311 drives a current 302 through wire 301 and generates a magnetic field around wire 301 creating circular magnetic field lines as indicated by arrow 303. Electrons and ions of plasma 107 follow helical paths around the magnetic field line indicated by arrow 303, thus confining plasma 107 in the shape of a toroid.

In some embodiments, current source 311 supplies a fixed current, and hence generates a static, circular magnetic field around wire 301. In this manner, the electrons and ions of plasma 107 are contained in the magnetic field surrounding wire 301.

In some other embodiments, current source 311 supplies a time-varying current, and hence generates a dynamic magnetic field. In this manner, the electrons and ions of plasma 107 are contained in the magnetic field surrounding wire 301 and are driven in alternate directions along the toroid.

In another embodiment, a plasma confinement circuit includes one or more wire coils wrapped in a toroidal configuration. Current passed through this coil, or coils, generates circular magnetic field lines as described with reference to FIG. 3, and similarly confines the sustained plasma.

In general, the elements employed to confine a sustained plasma (e.g., electrically conductive wire grids, wire coils, etc.) may be located within the plasma chamber containing the plasma or outside the plasma chamber. It may be advantageous to locate the confinement circuit elements outside of the plasma chamber to improve reliability. However, in some embodiments it may be desirable to locate elements of the confinement circuit within the plasma chamber in close proximity to the plasma to enhance the confining effect of the induced fields.

Confinement of a sustained plasma decreases the size of the plasma for a given pump energy, and thus increases radiance. However, confinement of the sustained plasma also enables a significant increase in radiance with increased pump energy. Without confinement, an increase in pump energy typically results in an increase in plasma size without a significant increase in radiance. However, by confining the sustained plasma, the additional pump energy results in a further increase in radiance. In some embodiments, the amount of accessible light generated by the plasma emission has a color temperature greater than 20,000 degrees Kelvin. In some embodiments, the amount of accessible light generated by the plasma emission has a color temperature greater than 30,000 degrees Kelvin.

In yet another aspect, one or more plasma confining circuits of a CSP light source confines the plasma to a substantially fixed size as the pump energy supplied to sustain the plasma is increased. By way of non-limiting example, a pump laser of a CSP light source is controlled to increase the plasma temperature of the plasma while the plasma is electrostatically confined using a spherically or cylindrically symmetric electric potential as described with reference to FIG. 1. In this manner the radiance and spectral distribution of the emission is controlled by changing the laser power while maintaining a small and uniform plasma shape. This results in a small and bright source of illumination light with tunable radiance and spectral distribution.

In a further aspect, a high radiance illumination source for use in semiconductor metrology includes a system or systems for igniting and sustaining a plasma, one or more plasma confining circuits that introduce an electric field, a magnetic field, or a combination of an electric field and a magnetic field to spatially confine the sustained plasma, and another system or subsystem to couple additional pump energy into the plasma.

Figure 4:
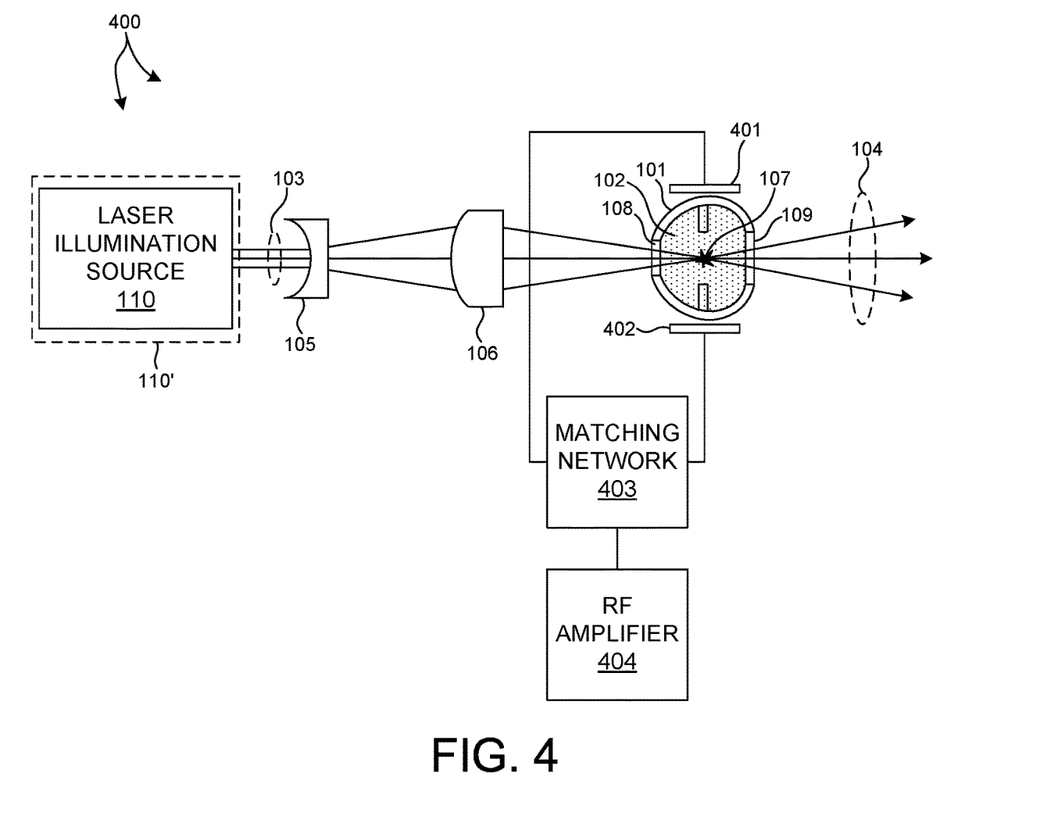
FIG. 4 depicts a CSP light source that includes a plasma pump circuit that delivers additional pump energy to a confined, sustained plasma in one embodiment.

FIG. 4 depicts a CSP light source 400 that includes a plasma pump circuit that delivers additional pump energy to a confined, sustained plasma in one embodiment. In the embodiment depicted in FIG. 4, like numbered elements are as described with reference to FIG. 1. As illustrated in FIG. 4, CSP light source 400 includes RF amplifier 404 coupled to a resonant matching network 403. The RF amplifier and the resonant matching network may include any suitable components known in the art. The resonant matching network is coupled to parallel plates 401 and 402 to create a relatively high strength oscillatory electric field. The plate capacitor may be arranged in any suitable configuration known in the art. The high frequency electric field couples additional energy into the confined, sustained plasma 107, enabling a further increase in radiance while the plasma 107 continues to be confined by a plasma confinement circuit, such as any of the embodiments described with reference to FIGS. 1-3. In this manner, the CSP light source 400 shown in FIG. 4 may be further configured as described herein. The embodiment of the CSP light source 400 shown in FIG. 4 may be included in any of the systems described herein.

Figure 5:
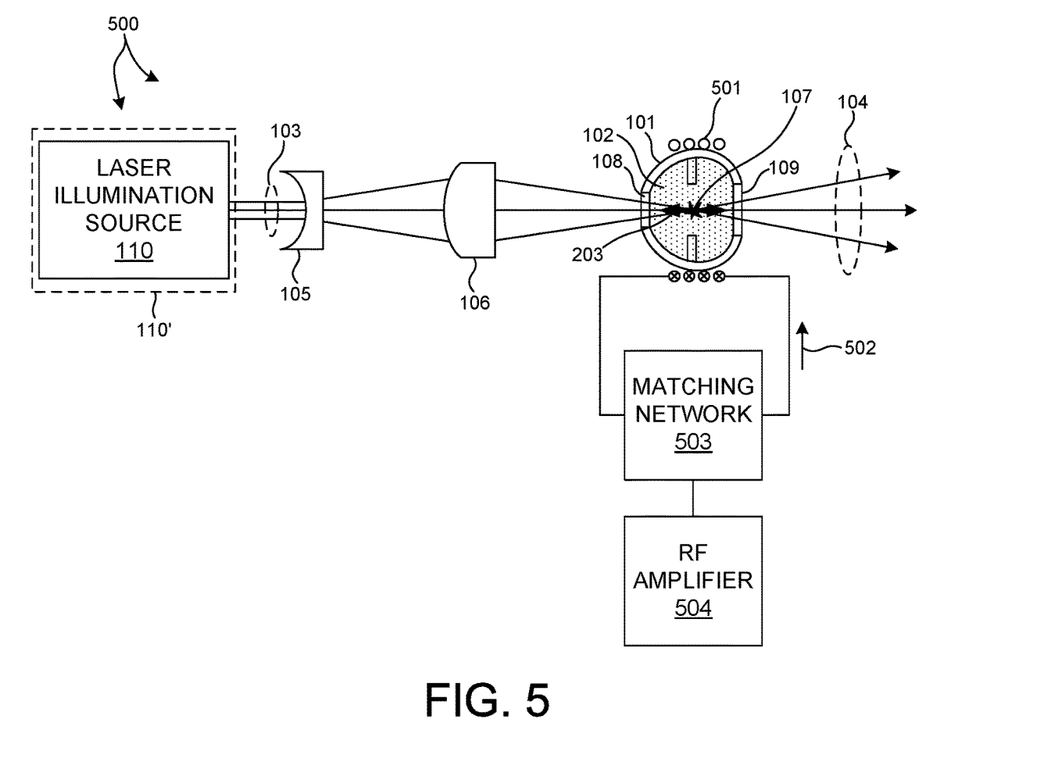
FIG. 5 depicts a CSP light source that includes a plasma pump circuit that delivers additional pump energy to a confined, sustained plasma in another embodiment.

FIG. 5 depicts a CSP light source 500 that includes a plasma pump circuit that delivers additional pump energy to a confined, sustained plasma in another embodiment. In the embodiment depicted in FIG. 5, like numbered elements are as described with reference to FIG. 1. As illustrated in FIG. 5, CSP light source 500 includes RF amplifier 504 coupled to a resonant matching network 503. The RF amplifier and the resonant matching network may include any suitable components known in the art. The resonant matching network may be configured to operate at about 50 ohms. The resonant matching network is coupled to coil 501 to create a relatively high strength oscillatory magnetic field. Coil 501 may be arranged in any suitable configuration known in the art. The high frequency magnetic field couples additional energy into the confined, sustained plasma 107, enabling a further increase in radiance while the plasma 107 continues to be confined by a plasma confinement circuit, such as any of the embodiments described with reference to FIGS. 1-3. In this manner, the CSP light source 500 shown in FIG. 5 may be further configured as described herein. The embodiment of the CSP light source 500 shown in FIG. 5 may be included in any of the systems described herein.

In some embodiments, RF or microwave power is capacitively coupled to the plasma to increase the plasma temperature, as described by way of non-limiting example with reference to FIG. 4, while employing inductively coupled magnetic fields to confine the plasma core to achieve high radiance, as described by way of non-limiting example with reference to FIG. 2 or 3.

In some other embodiments, RF power is inductively coupled to the plasma to increase the plasma temperature, as described by way of non-limiting example with reference to FIG. 5, while employing a spherically or cylindrically symmetric electric potential to confine the plasma core to achieve high radiance, as described by way of non-limiting example with reference to FIG. 1.

In general, any combination of one or more plasma confinement circuits and one or more plasma pump circuits as described herein may be combined to both confine and couple additional energy to a sustained plasma.

In another further aspect, a system or systems for sustaining a plasma and one or more plasma confining circuits of a CSP light source are modulated in combination to minimize plasma emission noise. Combining pump energy modulation with modulation of a plasma confining circuit (i.e., modulation of the plasma shape) generates a set of extended modulation frequencies to optimize stable photon emission radiance. Modulating the properties of the plasma at frequencies significantly greater than the Nyquist frequency of the system detector electronics reduces the sensitivity of the measurement to low frequency system noise. The modulation depth of the pump energy must be selected such that the pump power density does not reach a state where there is insufficient energy available to sustain the plasma.

In some embodiments, a pump laser and one or more plasma confining circuits of a CSP light source are modulated in combination to minimize plasma emission noise. However, in general, any system for sustaining and heating the plasma (e.g., inductively coupled systems, capacitively coupled systems, and laser pumped systems) can be modulated in combination with any system for confining the plasma (e.g., magnetic containment system and electrical containment system).

In yet another further aspect, a system or systems for confining a plasma may be employed to shape the plasma to avoid damage to elements of the CSP light source. For example, the plasma may be shaped by one or more plasma confining circuits to maintain a particular distance between the confined, sustained plasma and a window of the plasma chamber.

Figure 6:
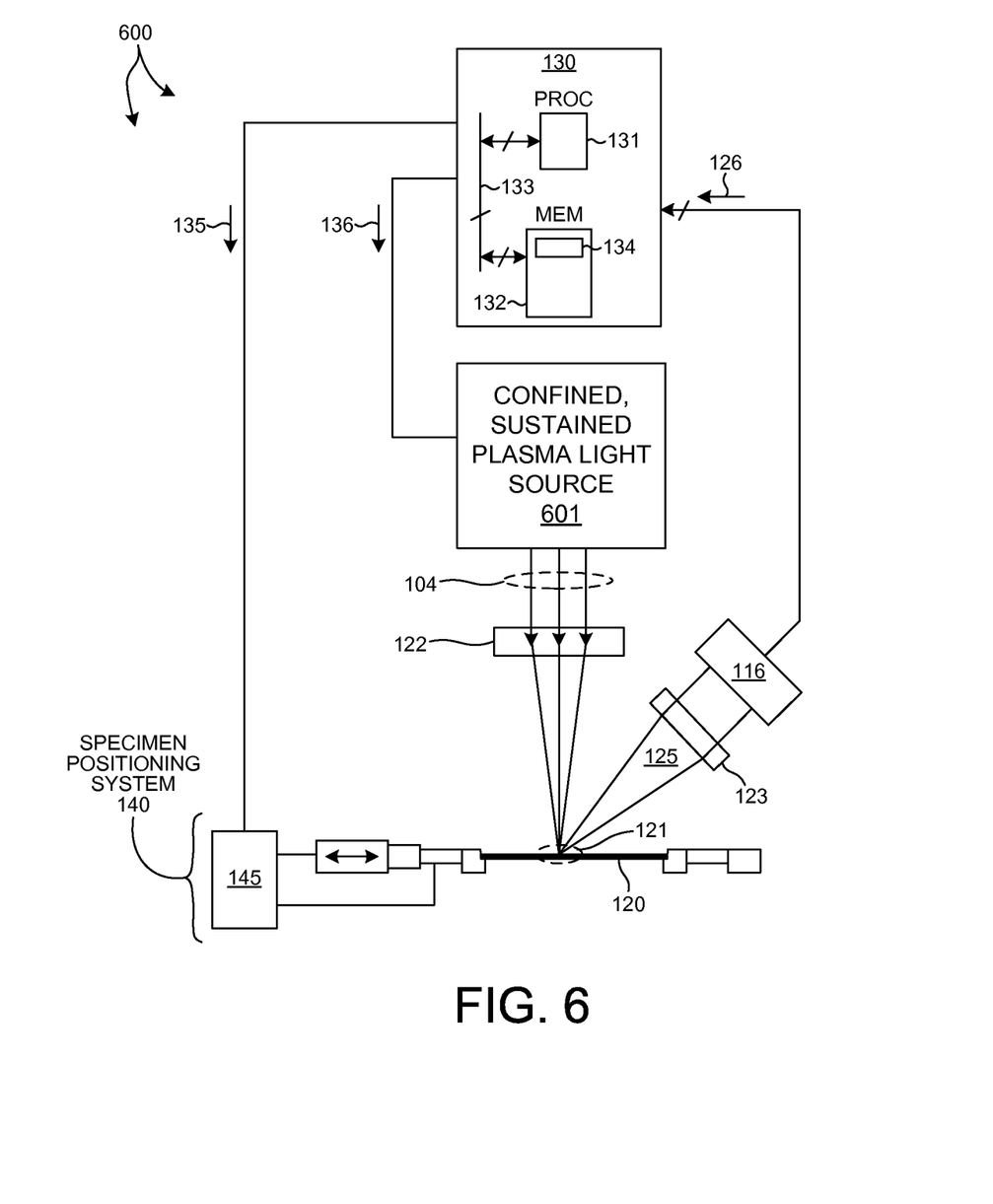
FIG. 6 illustrates a metrology tool 600 for measuring characteristics of a specimen that includes a CSP light source as described herein.

FIG. 6 illustrates a metrology tool 600 for measuring characteristics of a specimen that includes a CSP light source as described herein. As shown in FIG. 6, the system 600 may be used to perform optical scatterometry measurements over an inspection area 121 of a specimen 120 disposed on a specimen positioning system 140.

In general, and as depicted in FIG. 6, metrology system 600 includes CSP light source 601, beam shaping optics 122, collection optics 123, and detector 116. CSP light source produces illumination light 104 incident on inspection area 121 of specimen 120. In some embodiments, the CSP light source is configured to generate broadband radiation having wavelengths between 150 nanometers and 2,500 nanometers. Beam shaping optics 122 shape and direct incident illumination light 104 to specimen 120. In some embodiments, beam shaping optics 122 collimate or focus the illumination light 104 onto inspection area 121 of specimen 120. Collection optics 123 direct light from the specimen 120 to detector 116. The illumination and collection optics are designed to direct light from the plasma source to the measurement target and from the target to the detector, respectively, while controlling diffraction. This minimizes the amount of light that interacts with portions of the specimen outside of the measurement target. In some embodiments, beam shaping optics 122 and collection optics 123 include one or more collimating mirrors, apertures, monochromators, and beam stops, multilayer optics, refractive optics, diffractive optics, reflective optics, micro-electro-mechanical mirrors, diffusers, apodizers, polarizers, or any combination thereof. In particular, reflective optics may be utilized to eliminate chromatic aberration as well as high transmission efficiency, particularly in the extreme ultraviolet, vacuum ultraviolet, and deep ultraviolet spectral regions.

In the embodiment depicted in FIG. 6, detector 116 collects radiation 125 from specimen 120 and generates an output signal 126 indicative of properties of specimen 120 that are sensitive to the incident illumination light 104. Radiation 125 is collected by detector 116 while specimen positioning system 140 locates and orients specimen 120. Detector 116 is able to resolve one or more photon energies and produces signals for each energy component indicative of properties of the specimen. In some embodiments, the detector 116 includes any of a CCD array, a photodiode array, a CMOS detector, and a photomultiplier tube. In some embodiments, detector 116 is a wavelength dispersive detector, for example, in embodiments of system 600 implementing wavelength dispersive metrology. In some other embodiments, detector 116 is an energy dispersive detector, for example, in embodiments of system 600 implementing energy dispersive metrology.

Metrology system 600 also includes a computing system 130 employed to acquire signals 126 generated by detector 116, and determine properties of the specimen based at least in part on the acquired signals. As illustrated in FIG. 6, computing system 130 is communicatively coupled to detector 116. In one aspect, computing system 130 receives measurement data 126 associated with measurements of specimen 120 over an inspection area 121 illuminated by illumination light 104 generated by a confined, sustained plasma light source.

In one example, detector 116 is an optical spectrometer and measurement data 126 includes an indication of the measured spectral response of the specimen based on one or more sampling processes implemented by the optical spectrometer.

In a further embodiment, computing system 130 is configured to access model parameters in real-time, employing Real Time Critical Dimensioning (RTCD), or it may access libraries of pre-computed models for determining a value of at least one specimen parameter value associated with the specimen 120. In general, some form of CD-engine may be used to evaluate the difference between assigned CD parameters of a specimen and CD parameters associated with the measured specimen. Exemplary methods and systems for computing specimen parameter values are described in U.S. Pat. No. 7,826,071, issued on Nov. 2, 2010, to KLA-Tencor Corp., the entirety of which is incorporated herein by reference.

As illustrated in FIG. 6, metrology tool 600 includes a specimen positioning system 140 configured to both align and orient specimen 120 with respect the illumination source 601 and detector 116 of the metrology system 600. Computing system 130 communicates command signals 135 to motion controller 145 of specimen positioning system 140 that indicate the desired position of specimen 120. In response, motion controller 145 generates command signals to the various actuators of specimen positioning system 140 to achieve the desired positioning of specimen 120.

In one further aspect, metrology tool 600 includes a computing system (e.g., computing system 130) configured to communicate command signals 136 to CSP light source 601 to control plasma shape, temperature, spectral emission properties, or any combination thereof. In some examples, command signals 136 may include feedforward command signals (e.g., set-points) determined by computing system 130 based on a particular measurement application or system status. In some other examples, command signals 136 may include feedback command signals determined by computing system 130 based on measured properties of metrology system 600. By way of non-limiting example, metrology system 600 may include photodiodes to monitor power in one or more spectral regions at one or more locations in the optical path, spectrometers to monitor spectral intensity and profile characteristics, imaging sensors to characterize the beam profile, temperature sensors, pressure gauges and mass spectrometers to characterize the physical state of the plasma chamber, etc.

In response to command signals 136, system parameters are adjusted to alter plasma shape, temperature, spectral profile, or any combination thereof. For example, it may be desirable to alter the position and strength of emission peaks, brightness within a select wavelength band or bands, and overall spectral distribution (e.g., increased emissions in the UV at the expense of those in the infrared). In another example, it may be desirable to alter the plasma shape depending on the angle of incidence of the illumination light to more efficiently couple illumination light generated by the plasma to the beam shaping optics. In another example, it may be desirable to alter the plasma shape to optimize the beam profile incident on the sample to realize the smallest measurement box size.

In some embodiments, lamp fill pressure, fill contents (e.g. partial pressures), lamp temperature, or a combination thereof are altered based on command signals 136. In some embodiments, the pressure of working gas 102 is adjusted to influence the optical power density required to initiate a phase transition, the plasma size, and the ratio of broadband spectral output to output along atomic lines. In general, an increase in working gas pressure reduces the optical power density required to initiate a phase transition, confines the plasma size, and increases the ratio of broadband spectral output to output along atomic lines. In some embodiments, the average temperature of the working gas is adjusted to influence the optical power density required to initiate a phase transition from an ordinary state of matter into the plasma state and sustain the plasma state.

In some embodiments, the position of beam shaping optics in the illumination system such as MEMS mirrors, lenses, apodizers, or field stops are altered based on command signals 136.

In some embodiments, properties of the pump laser, such as wavelength, pumping NA, and pump power are altered based on command signals 136. Similarly, in some embodiments, properties of an inductively or capacitively coupled energy source, such as pump frequency and power are altered based on command signals 136.

It should be recognized that the various steps described throughout the present disclosure may be carried out by a single computer system 130 or, alternatively, a multiple computer system 130. Moreover, different subsystems of the system 100, such as the specimen positioning system 140, may include a computer system suitable for carrying out at least a portion of the steps described herein. Therefore, the aforementioned description should not be interpreted as a limitation on the present invention but merely an illustration. Further, the one or more computing systems 130 may be configured to perform any other step(s) of any of the method embodiments described herein.

In addition, the computer system 130 may be communicatively coupled to the detector 116 and the CSP light source in any manner known in the art. For example, the one or more computing systems 130 may be coupled to computing systems associated with the detector 116 and the CSP light source, respectively. In another example, any of the detector 116 and the CSP light source may be controlled directly by a single computer system coupled to computer system 130.

The computer system 130 of the metrology system 200 may be configured to receive and/or acquire data or information from the subsystems of the system (e.g., detector 116 and the CSP light source, and the like) by a transmission medium that may include wireline and/or wireless portions. In this manner, the transmission medium may serve as a data link between the computer system 130 and other subsystems of the system 600.

Computer system 130 of the metrology system 600 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 130 and other systems (e.g., memory on-board metrology system 600, external memory, or external systems). For example, the computing system 130 may be configured to receive measurement data (e.g., signals 126) from a storage medium (i.e., memory 132) via a data link. For instance, spectral results obtained using a spectrometer of detector 116 may be stored in a permanent or semi-permanent memory device (e.g., memory 132). In this regard, the spectral results may be imported from on-board memory or from an external memory system. Moreover, the computer system 130 may send data to other systems via a transmission medium. For instance, specimen parameter values determined by computer system 130 may be stored in a permanent or semi-permanent memory device (e.g., an external memory). In this regard, measurement results may be exported to another system.

Computing system 130 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 134 implementing methods such as those described herein may be transmitted over a transmission medium such as a wire, cable, or wireless transmission link. For example, as illustrated in FIG. 6, program instructions stored in memory 132 are transmitted to processor 131 over bus 133. Program instructions 134 are stored in a computer readable medium (e.g., memory 132). Exemplary computer-readable media include read-only memory, a random access memory, a magnetic or optical disk, or a magnetic tape.

By way of non-limiting example, FIG. 6 depicts a metrology system having normal incidence illumination and oblique angle detection for illustrative purposes. However, in general, any suitable combination of illumination incidence angle, or angles, and any suitable detection angle, or angles is contemplated within the scope of this patent document. For example, the illumination angle (i.e., angle of incidence) may be any angle, or combination of angles, ranging from normal incidence (i.e., aligned an axis normal to the surface of the specimen under measurement) to grazing incidence (i.e., less than ninety degrees from the surface normal). Similarly, the detection angle, may be any angle, or combination of angles, ranging from zero degrees (i.e., normal detection) to less than ninety degrees (i.e., oblique detection) from the surface normal.

As described with reference to FIG. 6, metrology system 600 includes an optical scatterometer system. However, in general, analysis based on one or more different metrology techniques may be contemplated within the scope of this patent document. Furthermore, measurements based on any metrology technique participating in a combined analysis may be performed on one or more individual metrology tools, one or more combined metrology tools, or any combination thereof without limitation.

In general, a confined, sustained plasma light source as described herein may be employed as a light source in any metrology, overlay, or inspection system where high signal to noise ratio and small target size is desirable. By way of non-limiting example, spectroscopic reflectometers, angle-resolved reflectometers, spectroscopic ellipsometers, bright and dark field imaging systems, or other optically based measurement techniques may benefit from a confined, sustained plasma light source as described herein. Other examples include a beam profile reflectometer that typically utilizes a high-numerical-aperture objective lens to focus illumination with a wide range of angles onto a small spot on the wafer; a multi-angle-of-incidence (AOI) ellipsometer that also requires relatively high NA; spectroscopic systems used for critical dimension metrology, overlay metrology, or metrology of process parameters such as lithography focus, based on a model-based fitting of measured signals or direct analysis of signal features benefit from a confined, sustained plasma source as described herein. These metrology applications benefit from the small emission volume and broad spectral range provided by a confined, sustained plasma light source. In some examples, a larger emission volume may be desirable. For example, in applications where a uniform illumination profile is required, the effective source size may be limited by a field stop. The light source should be sufficiently large to provide an acceptable level of intensity gradients across the field. To increase collected power, the size of the confined, sustained plasma is increased in a particular dimension without reducing plasma temperature by optimizing the plasma shape.

In some embodiments, a CSP light source may be implemented as part of a fabrication process tool. Examples of fabrication process tools include, but are not limited to, lithographic exposure tools, film deposition tools, implant tools, and etch tools. In this manner, the results of the metrology analysis are used to control a fabrication process. In one example, measurement data collected from one or more targets is sent to a fabrication process tool. The measurement data is analyzed and the results used to adjust the operation of the fabrication process tool.

Figure 7:
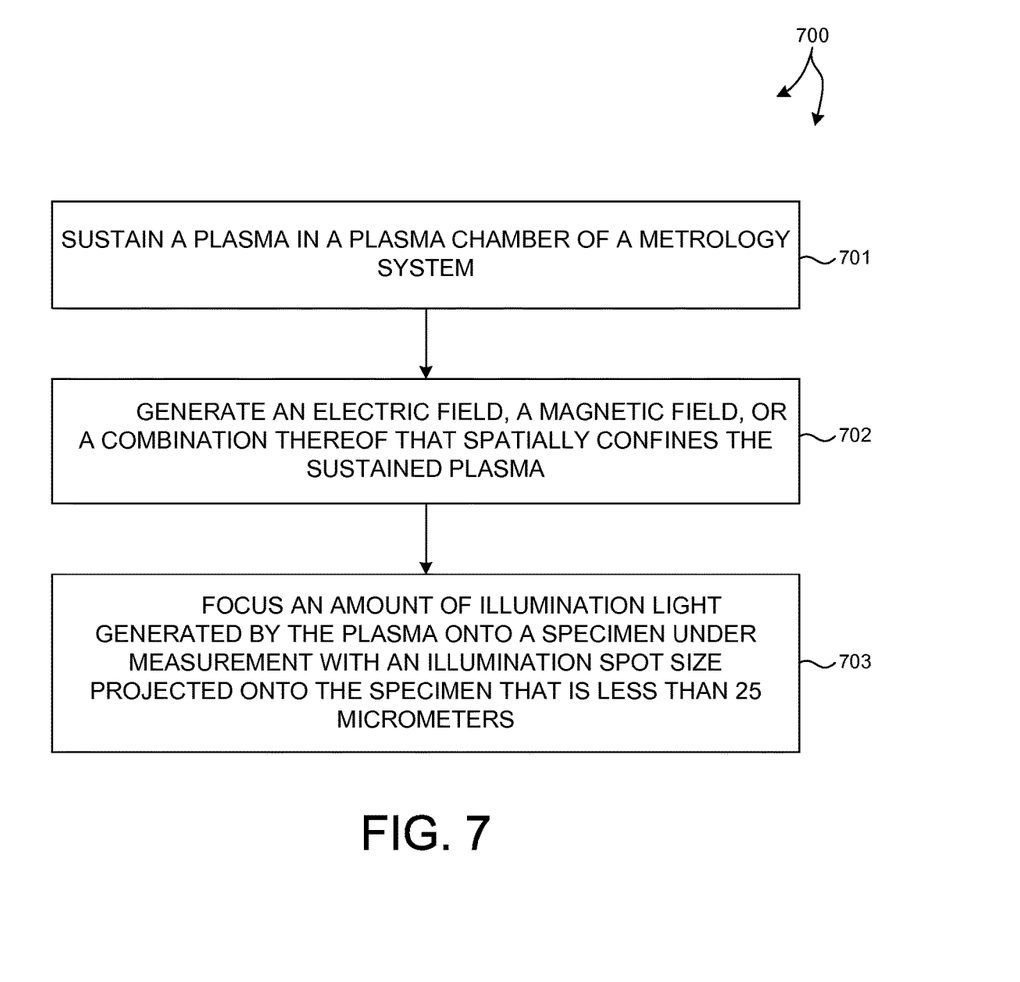
FIG. 7 is a flowchart illustrative of one exemplary method 700 suitable for generating high brightness, accessible illumination from a confined, sustained plasma.

FIG. 7 illustrates a method 700 suitable for generating a confined, sustained plasma in accordance with at least one inventive aspect. It is recognized that any data processing elements of method 700 may be carried out via a pre-programmed algorithm stored as part of program instructions 134 and executed by one or more processors of computing system 130.

In block 301, a plasma is sustained in a plasma chamber of a metrology system.

In block 302, an electric field, a magnetic field, or a combination thereof is generated to spatially confine the sustained plasma.

In block 303, an amount of illumination light generated by the plasma is focused onto a specimen under measurement. The illumination spot size projected onto the specimen is less than 25 micrometers.

In another aspect of the present invention, the illumination source used to ignite the plasma, sustain the plasma, or both, may include one or more lasers. In a general sense, the illumination source may include any laser system known in the art. For instance, the illumination source may include any laser system known in the art capable of emitting radiation in the infrared, visible, or ultraviolet portions of the electromagnetic spectrum. In some embodiments, the illumination source includes a laser system configured to emit continuous wavelength or pulsed laser radiation. In some embodiments, the illumination source may include one or more diode lasers. For example, the illumination source may include one or more diode lasers emitting radiation at a wavelength corresponding with any one or more absorption lines of the species of the gas of the plasma cell. In a general sense, a diode laser of the illumination source may be selected for implementation such that the wavelength of the diode laser is tuned to any absorption line of any plasma (e.g., ionic transition line) or an absorption line of the plasma-producing gas (e.g., highly excited neutral transition line) known in the art. As such, the choice of a given diode laser (or set of diode lasers) will depend on the type of gas utilized in the plasma cell of the present invention.

In some embodiments, the illumination source may include one or more frequency converted laser systems. For example, the illumination source may include a Nd:YAG or Nd:YLF laser. In other embodiments, the illumination source may include a broadband laser. In other embodiments, the illumination source may include a laser system configured to emit modulated laser radiation or pulse laser radiation.

In another aspect of the present invention, the illumination source may include two or more light sources. In one embodiment, the illumination source may include two or more lasers. For example, the illumination source (or illumination sources) may include multiple diode lasers. By way of another example, the illumination source may include multiple pulsed lasers. In a further embodiment, each of the two or more lasers may emit laser radiation tuned to a different absorption line of the gas or plasma within the plasma cell.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
   an illumination source configured to generate an amount of broadband radiation, wherein one or more beam shaping optics direct the amount of broadband radiation to a specimen, the illumination source comprising,
   a pump energy source configured to sustain a plasma at a plurality of different pump energy levels; and
   a plasma confining circuit configured to generate an electric field, a magnetic field, or a combination thereof that spatially confines the plasma sustained by the pump energy source to a substantially fixed size at each of the plurality of different pump energy levels; and a detector configured to receive an amount of radiation collected from the specimen in response to the incident radiation and generate signals indicative of a property of the specimen.

2. The metrology system of claim 1, wherein the plasma confining circuit comprises:

an electrically conductive wire; and a current source coupled to the electrically conductive wire, wherein the current source is configured to provide a current that flows through the electrically conductive wire to generate a magnetic field that confines the plasma sustained by the pump energy source.

3. The metrology system of claim 1, wherein the plasma confining circuit comprises:

a first electrically conductive wire grid;

a second electrically conductive wire grid, wherein the first electrically conductive wire grid is disposed within a volume of the second electrically conductive wire grid; and a voltage source coupled to the first and second electrically conductive wire grids, wherein the voltage source is configured to generate a voltage difference between the first and second electrically conductive wire grids that generates an electric field that confines the plasma sustained by the pump energy source.

4. The metrology system of claim 1, wherein the pump energy source is a continuous wavelength laser focused onto the plasma.

5. The metrology system of claim 1, further comprising:

a computing system configured to generate one or more command signals to modulate the pump energy source and the plasma confining circuit in combination.

6. The metrology system of claim 1, wherein an amount of accessible light generated by the plasma emission has a color temperature greater than 20,000 degrees Kelvin.

7. The metrology system of claim 1, wherein an illumination spot size projected onto the specimen is less than 25 micrometers.

8. The metrology system of claim 1, wherein the property of the specimen is overlay.

9. A method comprising:

sustaining a plasma in a plasma chamber of a metrology system;

generating an electric field, a magnetic field, or a combination thereof that spatially confines the sustained plasma; and focusing an amount of illumination light generated by the plasma onto a specimen under measurement, wherein the illumination spot size projected onto the specimen is less than 25 micrometers.

10. The method of claim 9, further comprising:

detecting an amount of radiation collected from the specimen in response to the illumination light; and generating one or more signals indicative of a property of the specimen.

11. The method of claim 10, wherein the property of the specimen is overlay.

* * * * *